United States Patent [19]

Nieuwenhuizen

[11] Patent Number: 5,753,457
[45] Date of Patent: May 19, 1998

[54] QUANTIFICATION OF ACTIVE PLASMINOGEN-ACTIVATOR-INHIBITOR-TYPE-1

[75] Inventor: Willem Nieuwenhuizen, CL Bunnik, Netherlands

[73] Assignee: Akzo Nobel N.V., Arnhem, Netherlands

[21] Appl. No.: 481,284

[22] PCT Filed: Jun. 28, 1994

[86] PCT No.: PCT/EP94/02127

§ 371 Date: Feb. 21, 1996

§ 102(e) Date: Feb. 21, 1996

[87] PCT Pub. No.: WO95/01452

PCT Pub. Date: Jan. 12, 1995

[30] Foreign Application Priority Data

Jun. 28, 1993 [EP] European Pat. Off. ............ 93201880

[51] Int. Cl.$^6$ ................ C12Q 1/06; G01N 33/53
[52] U.S. Cl. .................. 435/39; 435/4; 435/7.1; 435/7.91; 435/69.2; 435/24; 435/212; 435/975; 435/13; 435/39; 424/94.64
[58] Field of Search .............. 424/94.64; 435/7.1, 435/7.91, 413, 39, 212, 69.2, 975, 24

[56] References Cited

U.S. PATENT DOCUMENTS 5,520,911  5/1996  Anderson et al. .................. 424/94.64

FOREIGN PATENT DOCUMENTS

| 0 339 302 | 11/1989 | European Pat. Off. . |
| 0 450 086 | 10/1991 | European Pat. Off. . |
| WO 86/00413 | 1/1986 | WIPO . |
| WO 87/06346 | 11/1987 | WIPO . |
| WO 89/00005 | 1/1989 | WIPO . |
| WO 93/23561 | 11/1993 | WIPO . |

OTHER PUBLICATIONS

Declerck et al., "Measurement of Plasminogen Activator Inhibitor 1 (PAI-1) In Plasma with Various Monoclonal Antibody-Based Enzyme-linked Immunosorbent Assays", Thrombosis Research 1990, Supplement X, 3–9, Jan. 1, 1990.

Harpel et al., "Thrombospondin Forms Complexes with Single-Chain and Two-Chain Forms of Urokinase", J. Biol. Chem. 1990, 265, 11289–11294, Jul. 5, 1990.

Schleef et al., "Immunoradiometric Assay to Measure the Binding of a Specific Inhibitor to Tissue-Type Plasminogen Activator", J. Lab. Clin. Med. 1985, 106, 408–415, Nov. 1985.

M. Philips et al., *Thrombosis and Haemostasis*, 68(5):486–494 (1992).

P. Morton et al., *The Journal of Biological Chemistry*, 264:13:7228–7235, 1989.

R. Bos et al., *Fibrinolysis*, 6:173–182 (1992).

R. Bos et al., *Blood Coagulation and Fibrinolysis*, 3:303–307 (1992).

J. Chmielewska et al., *Clin. Chem.*, 32(3):482–485 (1986).

*Primary Examiner*—John Kight
*Assistant Examiner*—Friedrich N. Burnett
*Attorney, Agent, or Firm*—William M. Blackstone

[57] ABSTRACT

A method for the quantification of active plasminogen-activator-inhibitor-type-1 (PAI-type-1) presence in a sample, a method for preparing a reference curve for use in the quantification, a kit for carrying out the method for quantification and a carrier such as a microtiter plate comprising immobilized antibody directed against plasminogen activator.

24 Claims, 4 Drawing Sheets

QUANTIFICATION OF ACTIVE PLASMINOGEN-ACTIVATOR-INHIBITOR-TYPE-1

This case was filed under 35 USC 371 as the national stage of International Application PCT/EP9402127 filed Jun. 28, 1994 published as WO95/01452 Jan. 12, 1995.

DESCRIPTION

A method for the quantification of active plasminogen-activator-inhibitor-type-1 (PAI-type-1) present in a sample, a method for preparing a reference curve for use in the quantification, a kit for carrying out the method of quantification and a carrier such as a microtitre plate comprising immobilised antibody directed against plasminogen activator.

The subject invention lies in the field of haemostasis. The subject invention is directed at a method for the quantification of active plasminogen-activator-inhibitor-type-1 (PAI-type-1) present in a sample. The subject invention is also directed to a method for preparing a reference curve for use in the quantification and as a kit for carrying out the method of quantification and is also directed to a carrier such as a microtitre plate comprising immobilised antibody directed against plasminogen activator.

BACKGROUND OF THE INVENTION

Thrombosis, the development of blood clots (thrombi) in veins and arteries forms a serious complication of vascular diseases and is often the cause of an acute myocardial infarction. Thrombosis can be prevented in two ways, by preventing or decreasing the activation of the clotting system and the blood platelets or by activating the so-called fibrinolysis system in such a manner that the forming clot is degraded as fast as it is formed. The inner cellular layer of arteries and veins, the so-called endothelium plays an important role in these processes. The endothelium provides proteins that inhibit the coagulation process and produces the various factors that prevent the aggregation of blood platelets. Furthermore the endothelium controls the degradation of a forming thrombus by constitutive secretion of the protein "tissue-type plasminogen activator", also indicated as "t-PA", a protein that activates the fibrinolysis process. t-PA can also quickly be released from storage pools in the endothelium and a relatively large fibrinolytic activity can be targeted to threatened sites within the vein or artery with subsequent prevention of formation of a thrombus.

The fibrinolysis system is also capable of dissolving a clot that has already formed. A known example of this last situation is treatment of an acute myocardial infarction with the fibrinolysis enzyme t-PA. This new clinical application has enjoyed great interest over the past few years. In contrast to using t-PA for thrombolytic therapy, relatively little research has been carried out directed at manipulations of the availability of endogenous (i.e. made by the body itself) circulating t-PA, despite observations that a lowered fibrinolytic capacity (mainly t-PA activity) in blood is related to an increased risk of thrombosis. Above all the fibrinolytic effect of t-PA is maximal if it is already present during coagulation, i.e. t-PA that is added later is a lot less effective. This also explains the high doses of t-PA required for thrombolytic therapy and reinforces the importance of a sufficiently high endogenous t-PA activity level. For prevention of thrombosis therefore not only inhibiting the coagulation process could be considered, but also increasing the availability of t-PA via stimulation of endogenous t-PA production.

t-PA circulating in the blood is produced by endothelial cells in the wall of the arteries or veins. These endothelial cells synthesize t-PA, show a basal secretion of t-PA (constitutive secretion) and also contain a cellular stock of t-PA that can be secreted upon stimulation of the endothelial cell (acute secretion, also known as "release"). Such a cellular t-PA stock is a very powerful local defence mechanism: local physiological triggers of thrombus development (for example thrombus degradation products) will result in a strongly increased acute secretion of t-PA. The activity of t-PA in blood is, however, not only determined by the amount of t-PA but also by the amount of a specific inhibitor for t-PA, the so-called plasminogen-activatorinhibitor-type-1 (PAI-type-1). PAI-type-1 in plasma is also synthesized amongst others by the endothelium.

The availability of t-PA activity in the circulation or its fast recruitment from endothelial cells of the blood vessel during formation of blood clots is an essential parameter for fibrinolysis. Shortages of t-PA activity may cause thrombosis; excess t-PA activity may result in bleeding tendencies.

As the activity of t-PA is coupled to the presence of PAI-type-1 the level of PAI-type-1 in blood or plasma is an important parameter to determine the fibrinolytic capacity of a patient. Determination of the level of PAI-type-1 in blood or plasma could be useful for diagnosis of certain defects or for following the effects of treatment with certain drugs, for example drugs for treating defects in the fibrinolytic system.

The PA-inhibitor-type-1 (PAI-type-1) is the most important inhibitory protein controlling fibrinolysis via tissue-type plasminogen activator. This inhibitor was identified in 1982 and its activity can be measured through titration with t-PA that can be measured with the procedure described in Dutch Patent Application 8201987. The plasminogen-activator-inhibitor-type-1 specifically inhibits plasminogen activator activities, (t-PA and urokinase) in particular those of tissue-type plasminogen activator. The reactivity with tissue-type plasminogen activator is a lot higher than with urokinase. Plasminogen-activator-inhibitor-type-1 can be present in a sample in various molecular forms. It can be present in the active form, it can be present as a complex with plasminogen activator, said plasminogen activator being either t-PA or u-PA and it can also be present in the latent or inactive form. In blood about 30% of plasminogen-activator-inhibitor-type-1 can be present in the latent form. This can be a disturbing factor in determining the amount of active PAI-type-1 that is present in blood or plasma through immunological techniques even though only extremely rough treatment of a sample will actually result in activating said latent form. Plasminogen-activator-inhibitor-type-1 has been isolated from endothelial cell media as described by Van Mourik et al (J. Biol. Chem. 259 (1984) pp 14914–14921). An antiserum was developed by immunization of rabbits and purification of the IgG's with Protein A Sepharose (Pharmacia, Uppsala, Sweden).

Figure 1:
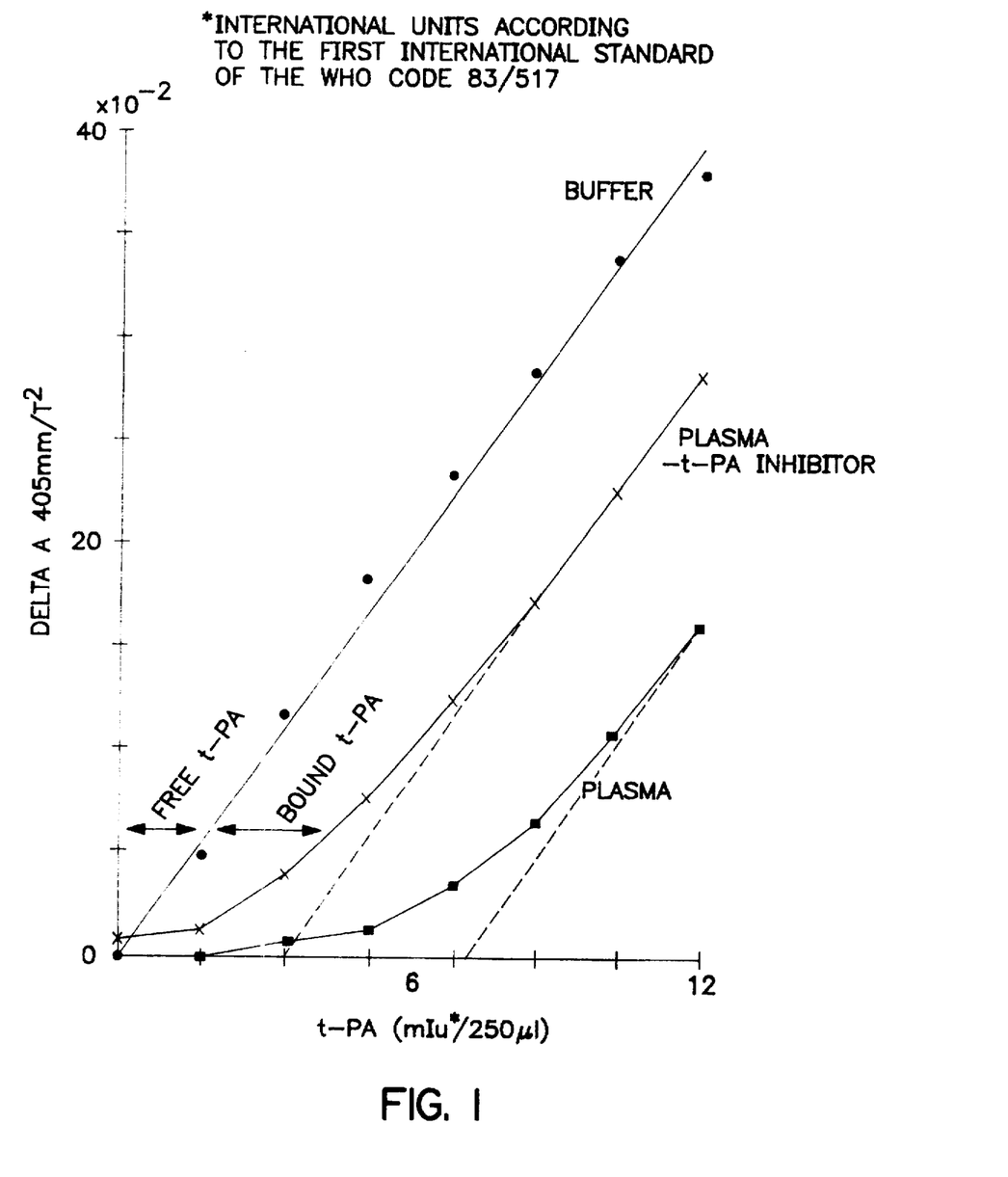
FIG. 1 illustrates how the addition of 20 μl of plasma gives a curve that upon extrapolation to the X-axis reveals the amount of inhibition expressed in an amount of neutralized t-PA.

A measurement for t-PA inhibitory activity can be carried out as described in Dutch Patent Application 8201987 where a titration is carried out on a sample, for example plasma comprising inhibitor, by titrating with a series of t-PA concentrations. The t-PA activity is measured by applying the usual t-PA measuring method (as described in said Patent Application) and FIG. 1 illustrates how the addition of 20 μl of plasma gives a curve that upon extrapolation to the X-axis reveals the amount of inhibition expressed in an amount of neutralised t-PA. This is an indirect method for determining the activity of tissue-type plasminogen activator in which method a sample is incubated with plasminogen and a stimulator for converting plasminogen to plasmin using tissue-type plasminogen activator (t-PA) as well as a substrate for plasmin, leading to a detectable reaction product upon reaction with plasmin. This known method is extremely laborious and also relatively inaccurate. Therefore a method is required which is more accurate and easier to carry out. The known method also requires dilution of the sample, which can lead to an initially unstable [(t-PA)-(PAI-type-1)] complex. Furthermore, the known method only gives an indication of the activity of the PAI-type-1 and does not lead to a direct value for or give an indication of the total amount of active PAI-type-1, expressed for example in micrograms. The subject method is directed at to solving the above-mentioned problems.

In EP 0 450 086 A1 an assay method for an active PAI is described. This method comprises assaying by an immunological assay method based on the sandwich method respectively (A) the human tissue plasminogen activator-human plasminogen inhibitor complex ([(t-PA)-(PAI)] complex) existing in a human specimen and (B) a human tissue plasminogen activator-plasminogen inhibitor complex ([(t-PA)-(PAI)] complex) existing in the human specimen to which a human tissue plasminogen activator (t-PA) was added and assaying the amount of the active human plasminogen activator inhibitor (PAI) based on the difference of the assay values, said method comprises (a) using as a first antibody a monoclonal antibody against a human plasminogen activator inhibitor (PAI) linked to an insoluble solid carrier having a specular surface, (b) using as a second antibody a polyclonal antibody against a human tissue plasminogen activator labeled with an enzyme, and (c) using as a detergent a detergent containing non-ionic surfactant having a HLB (hydrophile lipophile balance) value of at least 16. The synergistic influences of use of a monoclonal antibody against PAI as a first antibody, namely the immobilized antibody, and an enzyme labeled polyclonal antibody against t-PA as a second antibody in combination with the use of a solid carrier for the immobilization of the first antibody, said carrier having an extremely smooth surface and the use of a detergent containing a non-ionic surfactant having a HLB value of at least 16 purportedly reduces the non-specific adsorption of many proteins existing in the human specimen, particularly t-PA, PAI and the like to the solid carrier to the utmost, and also inhibits the non-specific adsorption of the second antibody so that components unnecessary for the immune reaction can effectively be washed and removed.

In particular, two monoclonal antibodies used for immobilizing PAI are described, namely JTI-3 and JTI-4 with a preference being expressed for JTI-4. The monoclonal antibody JTI-3 against PAI belongs to the subclass IgG$_f$ and recognizes an antigenic determination site such that even when t-PA is linked to PAI, even in a [(t-PA)-(PAI)] complex, its linkage to PAI is not inhibited, however when the monoclonal antibody is linked to PAI, the subsequent linkage of t-PA to PAI is inhibited.

The monoclonal antibody JTI-4 against PAI belongs to the subclass IgG$_f$ and its linkage to PAI is not inhibited when PAI is linked to t-PA. The specular surface is defined as being a surface having a center line average roughness (Ra) of 1.5 µm or less. Examples of such a surface are polystyrene beads and glass beads. It is described that the use of a surfactant in the assay system reduces non-specific adsorption, however only the non-ionic surfactants having a HLB of at least 16 do not inhibit the immune reaction as well. They only purportedly inhibit the non-specific adsorption of substances not involved in the immune reaction and the labeled antibody. Tween 20 with a HLB of 16.7 is given as a suitable example. It is further described in the European patent application that the presence of a protein having a molecular weight of 16,000 to 15,000 and an isoelectric point of 1.0 to 5.0, preferably with a molecular weight of 20,000 to 46,000 and an isoelectric point of 1.2 to 4.8 in the immune reaction solution further inhibits non-specific adsorption and thus remarkably lowers the background, thereby easily allowing further high sensitivity. Examples of such a substance are given, for example casein and pepsin.

Figure 2:
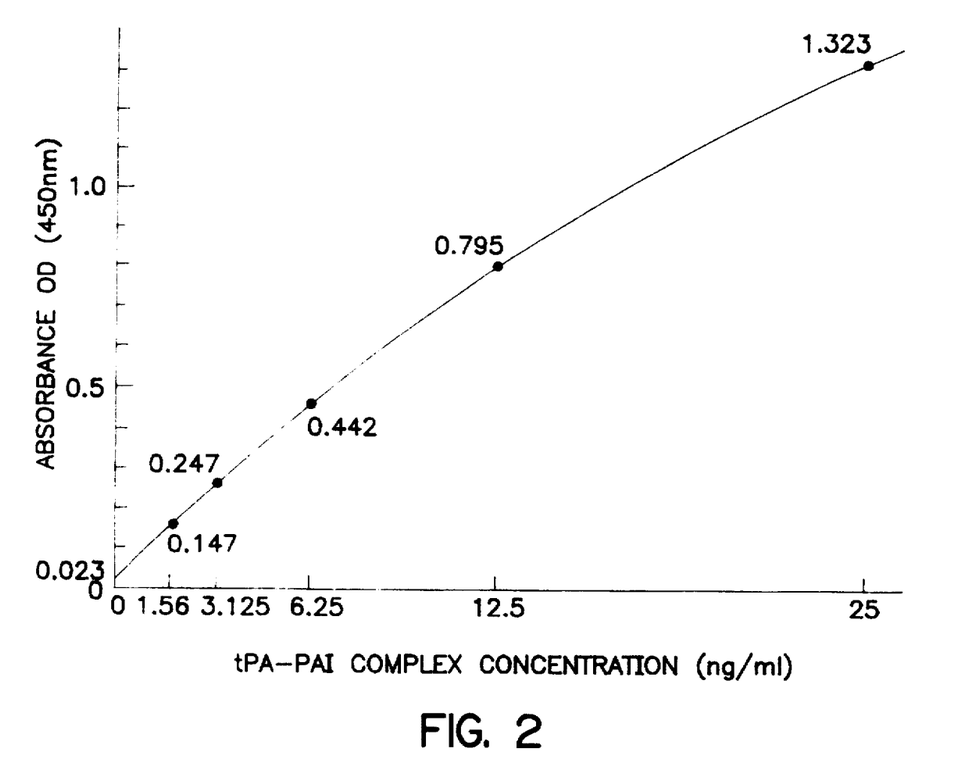
FIG. 2 illustrates a calibration curve for the immunological assay of the [(t-pA(-(PAI)] complexes disclosed in EP-0 450 086, which indicates a relationship between the concentration of the [(t-PA)-(PAI)] complex and absorbance.

FIG. 2 denotes a calibration curve for the immunological assay of the [(t-PA(-(PAI)] complex as disclosed in EP-0 450 086 and denotes a relation between the concentration of the [(tPA)-(PAI)] complex and absorbance. From FIG. 2 it is apparent that an OD of approximately 0.3 corresponds to a [(t-PA)-(PAI)] complex concentration of approximately 4 ng/ml. The active PAI concentration can then be determined as the result of step A minus result B multiplied by 0.42. 0.42 is the ratio of the molecular weight of PAI to [(t-PA)-(PAI)]. So the OD of 4 ng/ml t-PA-PAI corresponds to 0.42×4 ng/ml active PAI.

The method disclosed in the European patent application 0 450 086 still exhibits a number of disadvantages and requires some undesirable measures. For example, the method according to the European patent application cannot simply be carried out in microtitre plates that are standardly available, as these will not have the required specular surface. This is undesirable for tests that are suitable to be preferably carried out using immune reactions, that are suitable for use with standard equipment, that are suitable for use with small amounts of sample, or that are suitable for being carried out in hospital laboratories. Besides this, the use of a monoclonal antibody directed against PAI for immobilizing PAI does not distinguish between latent PAI and active PAI and can only in specific cases distinguish between PAI complexed to t-PA and PAI forms not complexed to t-PA. In particular, this can be important in cases where platelet rich plasma is used as sample due to the fact that blood platelets comprise a relatively high proportion of latent PAI which can be released into the plasma and could thereby influence the results of the assay as described in the cited patent application leading to inaccuracy. The monoclonal antibody of preference JTI-4 has the characteristic that linkage thereof to PAI is not inhibited even when PAI is already linked to t-PA. In addition apparently no mention is made of it being able to distinguish between latent and active PAI. This means that all forms of PAI present in a sample will be immobilized resulting in competition for the immobilization sites between various forms of PAI, with a large percentage not being the form one wishes to detect and consequently the sensitivity for detection of immobilized complexes of [(t-PA)-(PAI)] will be reduced. The other monoclonal antibody JTI-3 illustrated in the European patent application is also incapable of distinguishing between various forms of PAI. A further aspect of the cited assay leading to inaccurate results lies is the fact that from the moment of taking the sample to carrying out the test the reaction of t-PA to PAI thereby forming [(t-PA)-(PAI)] complex can continue, which influences the outcome of step A–B and thereby renders the test inaccurate. For samples from normal donors, this can mean an error of 10 to 20% in the value of active PAI. In particular, for plasma from donors having an increased level of t-PA the error will become even larger. The method described in the cited European patent application wherein the monoclonal antibody JTI-3 is used must be carried out in two steps, i.e. the reaction of PAI with t-PA must occur exogenously before the mixture is contacted with the immobilized monoclonal antibody as after binding of PAI to monoclonal antibody JTI-3 no linkage to t-PA occurs and thus reduced detection of potentially active PAI is possible. Obviously an assay capable of being carried out in one step and in one container is to be preferred. Finally, the cited method does not meet the criteria set by the Scientific and Standardization Committee (SSC) of the International Society of Thrombosis and Haemostasis (ISTH) for a reference method. The criteria for SSC reference methods are the following: The immune- and activity-depleted samples should be negative; there should be a good linearity of the assay with the PAI-1 concentration; the assay should not detect PAI-2 and PAI-3, and the change resulting from addition of t-PA to STABILYTE plasma should be less than 20%. STABILYTE plasma is plasma that has been treated in such a manner that reaction between t-PA and PAI resulting in complex formation cannot occur.

The subject invention is directed to an assay and a kit for carrying out said assay which solve the above mentioned problems. In particular this is the first assay to our knowledge that in fact can commercially meet the criteria of the SSC and can be used for assaying samples from donors with abnormally high t-PA levels as well as samples from normal donors. The test described in the cited European patent application 450 086 will not meet the requirements of the SSC as it is not suited for accurate determination in samples with higher levels of t-PA than normal.

SUMMARY OF THE INVENTION

The subject invention lies in the field of hemostasis. The subject invention is directed to a method for the quantification of active plasminogen-activator-inhibitor-type-1 (PAI-type-1) prevent in a sample. The subject invention is also directed to a method for preparing a reference curve for use in quantification, a kit for carrying out the method of quantification and a carrier such as a microtiter plate comprising immobilized antibody directed against plasminogen activator.

DESCRIPTION OF THE PREFERRED EMBODIMENTS

The subject invention is directed to a method for the quantification of active plasminogen-activator-inhibitor-type-1 (PAI-type-1) present in a sample comprising taking two portions from the sample and carrying out at least the following steps:

a) determining in one portion a value corresponding to the total amount of complex between PAI-type-1 and plasminogen activator (PA), the so-called [(PA)-(PAI-type-1)] complex with plasminogen activator (PA) already present at the moment of sampling and b) calculating from the value determined in step a) the amount of [(PA)-(PAI-type-1)] complex present at the moment of sampling;

c) determining in the other portion a value corresponding to the total amount of [(PA)-(PAI-type-1)] complex present after addition of an excess of the active form of tissue-type plasminogen activator (t-PA) to said portion and d) calculating from the value determined in step c) the amount of [(PA)-(PAI-type-1)] complex present after the addition of the excess t-PA;

e) subtracting the total amount of complex as determined in b) from the total amount of complex as determined in d) resulting in the amount of active PAI-type-1 that was present at the moment of sampling in a volume of the sample equivalent to the volume of the portion characterized in that the portion of step a) is contacted with means for inhibiting complexation of PA with PAI from the moment of sampling through step a) and step a) comprises contacting the portion with at least one immobilised capturing agent, said immobilised capturing agent i) being directed at PA, preferably at PA of the [(PA)-(PAI-type-1)] complex and ii) being present in an amount and with a specificity sufficient for the molecular forms of PA, preferably of the [(PA)-(PAI-type-1)] complex present in the portion to be complexed to said capturing agent and contacting the portion with at least one tagging agent, said tagging agent i) preferably being provided with a detectable marker, ii) being directed at PAI preferably at PAI of the [(PA)-(PAI-type-1)] complex and iii) being present in an amount and with a specificity sufficient for the molecular forms of PAI-type-1 present in the portion to be complexed to said tagging agent and subsequently after carrying out appropriate incubation and washing steps determining a value corresponding to the amount of detectable marker that has been immobilised by binding to immobilised capturing agent and step c) comprises contacting the other portion with an excess of the active form of t-PA, thereby allowing non bound active PAI-type-1 present in the portion before the addition to form [(t-PA)(PAI-type-1)] complex and also contacting this portion with tagging agent and capturing agent as elaborated in step a), subsequently determining a value corresponding to the amount of detectable marker that has been immobilised by binding to the immobilised capturing agent.

In step c) virtually all active plasminogen-activator-inhibitor type 1 (PAI-type-1) present in the sample will react with the excess t-PA to form a complex. Virtually all in this context implies at least 90%.

Contacting the portions with tagging agent and capturing agent is preferably carried out concomitantly with a view to eliminating the number of operations and reducing the amount of reagents required for an assay, in other words to carrying out a one step assay in steps a) and c) of the method according to the invention as disclosed above. Both tagging agent and capturing agent can be antibodies and either one or both can be polyclonal and/or monoclonal antibodies. A preference exists for a monoclonal capturing agent.

Care must be taken to prevent that the means for ensuring that the complexation of PA and PAI is inhibited interfere with the capturing and/or tagging steps of the assay. Alternatively additional means must be taken to counteract the inhibition, thereby rendering capturing or tagging steps of the assay possible whilst still being able to counteract the [(PA)-(PAI)] complex formation in step a). Furthermore, if the sample is subjected to the means for inhibiting complexation at the moment of sampling prior to splitting into the two portions it is necessary for the means to be reversible or counteracted in the portion to be used for step c) as step c) requires complex formation. For clinical practice it is preferable to sample and subject the whole sample to the means for ensuring inhibition followed by splitting into portions for steps a) and c) rather than immediately at the moment of sampling splitting into two portions which are subjected to different treatment at that particular moment. In particular, when immune reactions are involved in the capturing and/or tagging steps quite specific reaction media are required for good and fast immune reaction. The media required are well-known to a person skilled in the art of immune reactions. By way of example to illustrate the outlined principle in an embodiment of the invention the sample can at the moment of sampling be contacted with a medium with a pH sufficiently low to inhibit complexation between PA and PAI. This inhibition of complexation should occur as soon as possible after the sampling has occurred in order to minimize the inaccuracy that will be caused if PA can react further with PAI after sampling. Naturally a sample of blood taken from a subject will be put in a medium with anticoagulation properties as is usual in this sort of assay. A citrate comprising medium having an acid pH is an extremely suitable medium with which the sample can be contacted due to the fact that this medium fulfils both the afore-mentioned goals of inhibition of complexation and anticoagulation. STABILYTE tubes comprising amongst other components citrate in a sufficient amount are commercially available and suitable. STABILYTE tubes have an additional bonus as they inhibit blood platelets from releasing their contents. As blood platelets comprise an extremely high percentage of latent PAI this measure reduces inaccuracy possibly due to detection of latent PAI. This can be particularly relevant when testing platelet rich samples. However, as such an acidic medium is not conducive to carrying out immune reactions the capturing and/or tagging steps of the assay cannot be carried out. In order therefore to overcome this problem additional means must be taken, thereby rendering the medium suitable for carrying out the immune reactions without sacrificing the inhibition of complex formation. It has been found that the addition of buffer which increases the pH to an acceptable level for carrying out immune reactions, and which comprises a small inhibitor of PA, in particular t-PA, such as PPACK (H-D-Phe-Pro-Arg-CMK) to prevent complex formation, is capable of fulfilling the desired requirements for the portion to be used in step a). In addition the portion to be used in step c) can also be subjected to contact with means to restore the pH to a level at which the [(PA)-(PAI)] complexation can occur. Addition of e.g. phosphate buffer to the portion to be used in step c) to counteract the acidic pH is a suitable means of achieving the desired objective for portion c), i.e. enabling complexation of PA and PAI. The addition of a buffer altering the acidic pH of the portion to be used in step a) to a level at which immune reactions can effectively take place is an effective means of reaching the desired objective, however other means must be take to ensure continued inhibition of complex formation of [(PA)-(PAI-type-1)] complex. An inhibitor of PA can be added for maintaining the situation at the moment of sampling with regard to the amount of [(PA)-(PAI)] complex present then. Phosphate buffer has been presented by way of example but any number of acidity reducing media can be used and will be clear to a person skilled in the art. Also a number of inhibitors of PA, in particular t-PA and u-PA are known.

The method according to the invention preferably comprises a one step EIA in steps a) and c). The use of polyclonal antibody against PAI as tagging agent in steps a) and c) is a suitable embodiment. The capturing agent is suitably a monoclonal antibody.

A suitable example of the quantification method according to the invention thus comprises using an antibody directed against PAI-type-1 as tagging agent and an antibody ($ab_{t-PA}$) capable of binding different molecular forms of t-PA such as single chain t-PA, double chain t-PA or [(t-PA)-(PAI-type-1)] complex as immobilised capturing agent.

As already stated in the introductory part the plasminogen-activator-inhibitor-type-1 can bind to tissue-type plasminogen activator t-PA as well as to urokinase. Generally the main interest will be directed at the reaction of PAI-type-1 with t-PA with the reaction of PAI-type-1 with urokinase being of subsidiary interest. There are, however, certain exceptional instances where the presence of urokinase can give a large contribution to the total amount of PAI-type-1, namely in cases where a patient has a high amount of urokinase in his or her blood or plasma (such as during thrombolytic therapy with u-PA). In these instances obviously it is essential in order to determine the amount of active PAI-type-1 using the method according to the invention to also include an antibody directed against urokinase in order to prevent large inaccuracy in the result. Normally, however, use of the second antibody directed against urokinase will not be required, as the influence of not including u-PA that has bound PAI-type-1 is negligible in normal cases due to the much higher reactivity of PAI-type-1 with t-PA than with u-PA. Furthermore u-PA is usually present as inactive precursor (sc-uPA) which is incapable of reacting with PAI-type-1 and must first be converted to (tc-u-PA).

The subject method can therefore further comprise in step a:

contacting the portion with a capturing agent comprising antibody capable of binding different molecular forms of tissue-type plasminogen activator, such as single chain (t-PA), double chain t-PA or the complex [(t-PA)-(PAI-type-1)] and also contacting the portion with a second capturing agent, said second capturing agent comprising antibody capable of binding different molecular forms of urokinase plasminogen activator, such as single chain (u-PA), double chain u-PA or the complex [(u-PA)-(PAI-type-1)]. The two types of antibody can be immobilized on the same carrier. The sample can be concomitantly contacted with both types.

With the steps a) and c) of this embodiment of the method according to the invention values corresponding to the amount of [(t-PA)-(PAI-type-1)] complex plus [(u-PA)-(PAI-type-1)] complex can be determined. In particular an antibody directed against molecular forms of PA to be used in the subject method binds at least to the molecular form of PA of the corresponding [(PA)-(PAI-type-1)] complex.

The corresponding tagging agent in this embodiment can be an antibody ($ab_{PAI-type-1}$) directed against PAI-type-1 of the [(PA)-(PAI-type-1)] complex. In particular an antibody is used directed against the molecular form of PAI-type-1 present in the [(PA)-(PAI-type-1)] complex.

Depending on the objective of the determination carried out by the method according to the invention as described above, one can use values obtained in steps a) and c) to compare plasmas of various donors or to follow a certain donor's reaction to a specific drug. These objectives can be achieved by carrying out the method according to the invention a few times over a certain period of time before, during and after treatment with a specific drug or simply in periodic checkups in which the values that have been obtained in steps a) and c) for each check-up, can be compared with the values from previous check-ups.

It is also possible to derive from these values the molar amount of active PAI-type-1 present in the plasma or blood via steps b), d) and e). This can be achieved by comparing the results obtained in steps a) and c) with a reference curve. Therefore the method according to the subject invention can further comprise in steps b) and d) calculating the amounts of [(PA)-(PAI-type-1)] complex from the respective values obtained in steps a) and c) by comparison of said respective values with corresponding values on a reference curve, said reference curve being a plot of known concentrations of [(PA)-(PAI-type-1)] complex against the corresponding value of marker detectable marker.

Said reference curve can be obtained by carrying out step a) and/or c) with at least one reference sample comprising a specific known concentration of [(PA)-(PAI-type-1)] complex and/or one or more dilutions of said reference sample, thereby obtaining at least two values corresponding to two specific concentrations of [(PA)-(PAI-type-1)] complex and plotting the thus determined values against their respective known concentrations. The known concentration of [(PA)-(PAI-type-1)] can be provided by the manufacturer of the reference sample. It is also possible that the concentration of [(PA)-(PAI-type-1)] of the sample to be used as reference sample is unknown and must also be determined. In this case the concentration of [(PA)-(PAI-type-1)] of the reference sample can be determined for example in a manner comprising the following steps:

1) subjecting the reference sample to conditions such that at least virtually all t-PA present in the reference sample is converted to [(t-PA)-(PAI-type-1)] complex, 2) making a serial dilution of the mixture resulting from step 1) resulting in subsamples, 3) contacting the subsamples formed in step 2) with at least one immobilised capturing agent for one of the components of [(PA)-(PAI-type-1)] complex, resulting in immobilised [(PA)-(PAI-type-1)] complex, 4) contacting immobilised complex from step 3) with at least one tagging agent for one component of the immobilised complex, preferably the same component against which the tagging agent in steps a–d of the quantification method according to the invention is directed, said tagging agent also preferably being provided with the same detectable marker as used in steps a–d of the quantification method according to the invention, 5) measuring each subsample to obtain the value corresponding to the amount of immobilised detectable marker (*) per subsample and 6) plotting the values obtained in step 5) against the amount of marker corresponding to said value, the amount of marker being derivable from a calibration curve for said marker and the component of the [(PA)-(PAI-type-1)] against which the tagging agent is directed. In the case of the reference sample comprising an initially unknown concentration of [(PA)-(PAI-type-1)] normal plasma is preferably used as this always comprises excess (PAI-type-1) thereby ensuring virtually all t-PA is in fact converted as required.

Virtually all in step 1 indicates that more than 90% of t-PA is converted to complex. Conditions suitable for converting virtually all t-PA present in the reference plasma as stated in step 1 are incubation for at least one hour at room temperature. The length of time of incubation is not critical. Incubation of 1–16 hours at room temperature for example is suitable.

This method for determining the concentration of [(PA)-(PAI-type-1)] complex of the reference sample as such and also this method in combination with the previously described embodiments for the quantification of active plasminogen activator-inhibitor-type-1 present in a sample form part of the subject invention.

In a specific example of the method for determining the concentration of [(PA)-(PAI-type-1)] complex of the reference sample the tagging agent is directed against different molecular forms of t-PA as already described in the quantification method for the capturing agent. Thus, in step 3) immobilised capturing agent for t-PA is used resulting in immobilised [(PA)-(PAI-type-1)] complex. Subsequently in step 4) the immobilised complex from step 3) is contacted with a tagging agent for the molecular form of t-PA comprised in the immobilised [(PA)-(PAI-type1)] complex. Preferably the tagging agent is provided with the same detectable marker as used in steps a) and c) of the method for the quantification of active plasminogen PAI-type-1 present in a sample. The amount of t-PA can then be determined using a calibration curve of pure t-PA of a known concentration in a manner well known to a person skilled in the art.

The method for determining the concentration of [(PA)-(PAI-type-1)] complex of the reference sample to be used for the method of quantification of active PAI-type-1 according to the subject invention can conveniently comprise carrying out any t-PA determination assay generally been known as suitable for determining the amount of the complexed form of t-PA (see for example Blood Coagulation and Fibrinolysis 3 (1992), 303–307 by Bos et al.).

In a specific embodiment they described it is possible to make the reference curve for t-PA-determination in a method comprising the following steps:

1) subjecting a sample of reference plasma to conditions such that virtually all t-PA present in the sample of reference plasma is converted to [(PAI-type-1)-t-PA] complex, 2) making a serial dilution of the mixture resulting from step 1) resulting in subsamples, 3) contacting the subsamples formed in step 2) with immobilised capturing agent for t-PA, resulting in immobilised complex [(t-PA)-(PAI-type-1)], 4) contacting the immobilised complex from step 3) with a tagging agent for at least the molecular form of t-PA as comprised in the immobilised [(t-PA)-(PAI-type-1)] complex, said tagging agent being provided with detectable marker, preferably the same detectable marker as used in the previous steps a) and c) of the quantification method as described, 5) measuring each subsample to obtain the value corresponding to the amount of detectable marker per subsample that has been immobilised and 6) plotting the values obtained in step 5) against the amount of marker calculated for said value, the calculation having been carried out on the basis of a measurement made of a known amount of t-PA against which the tagging agent of step 4) is directed. In the subject method the above described t-PA assay is used as a part of active PAI determination.

In the methods according to the invention antibodies directed against molecular forms of PA, said term comprising the molecular forms of both t-PA and urokinase can be monoclonal antibodies or polyclonal antibodies. Preferably an antibody directed against at least a molecular form of PA will bind at least to the molecular form of the corresponding PA complexed with PAI-type-1. A number of anti t-PA antibodies is available and the expert can easily determine which are suitable (Mc Gregor et al. Thromb. Haemostas, 53 (1985) 45; Matsuo et al., Thromb. Res. 51 (1989), 485 and Van Zonneveld et al., Thromb. Haemostas, 57 (1987), 82).

An antibody directed against PAI-type-1 ($ab_{PAI-type-1}$) that can be used in the methods according to the subject invention is obtainable from serum of a mammal injected with PAI-type-1. As described previously such antibodies are already available (Van Mourik et al.) and purified PAI-type-1 is also commercially available from American Diagnostica.

There are many examples of detectable markers that can be used in the methods according to the invention. For example radioactive markers, chromogenic markers with an enzyme having a chromogen as substrate and a chromophore as a product and fluorescent groups; there is a large number of such markers available to a person skilled in the art. A particularly suitable detectable marker is horseradish peroxidase. This is very often used as a marker in immunoassays. Any detectable marker that is usually used in an immunoassay is suitable for use in the methods according to the invention and will be obvious to a person skilled in the art.

Figure 3:
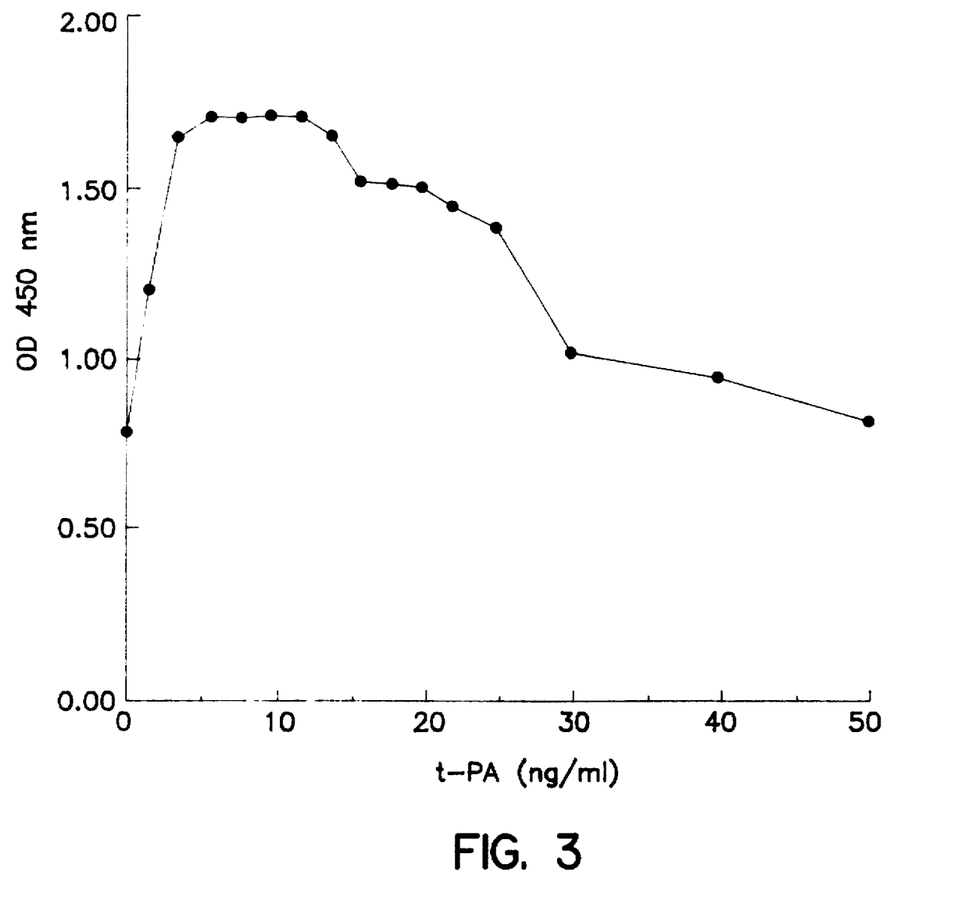
FIG. 3 illustrates that only amounts of excess t-PA greater than 20 ng/ml t-PA can cause complications in assaying for complexed t-PA.

The amount of immobilized tagging agent can be determined depending on the detectable marker that is used. Use of a chromogenic marker for example leads to determination of the value corresponding to the amount of tagging agent through determination of the optical density in a manner well known to a person skilled in the art. As already described, the value derived can be subsequently used to determine the amount of active PAI-type-1 for example in weight such as micrograms or in moles. With the subject method unexpectedly high sensitivity, high specificity in combination with high accuracy and precision are obtained. A number of factors capable of disturbing these characteristics in other tests have now been eliminated or counteracted. Free t-PA will not be detected only complexed t-PA. Too large an excess of t-PA could potentially be a complicating factor, but tests have shown that only amounts in excess of 20 ng/ml t-PA can cause problems (FIG. 3). This is a negligible problem in comparison to a test using an immobilized antibody against PAI. Preferably the subject method will be used with an amount of t-PA below 15 ng/ml in step c) to prevent any interference.

The capturing agent can be immobilized for the methods according to the invention, for example in a well of a microtitre plate in a manner well known in the art. No specific requirements as to the Ra of the surface are needed, i.e. super smooth surfaces are not required to ensure sufficient elimination of non-specific adsorption of protein in contrast to the method cited in EP-0 450 086. Many other methods of immobilizing antibodies are known and are suitable for immobilization in the methods according to the invention.

Another proposed embodiment for carrying out the method for quantification according to the invention comprises addition of antibody directed specifically against the complex [(PA)-(PAI-type-1)] to the portion in steps a) and c), said antibody being incapable of binding to other molecular forms of PA and PAI-type-1 and then determining the amount of antibody bound to the complex.

The antibody can for example be immobilized and be used as capturing antibody for the complex, in which case determination of the amount of immobilized complex with e.g. a tagging antibody directed at any of the components of the complex can be used, said tagging antibody being provided with a detectable marker.

Alternatively the complex can be immobilized with a capturing agent for PA and be contacted with the antibody directed specifically against the complex, said antibody functioning as tagging antibody and therefore being provided with a detectable marker.

Another aspect of the invention is provided by a kit comprising the required components for carrying out a method for quantification according to the invention as described above. Such a kit comprises at least one reference sample either with a known amount of the [(PA)-(PAI-type-1)] complex, or comprising normal plasma one container, with a carrier e.g. a microtitre plate, comprising at least one immobilized capturing agent directed against the PA component of the [(PA)-(PAI-type-1)] complex, or specifically at the complex as such rather than separate components thereof one container comprising at least one tagging agent directed against one of the components of the [(PA)-(PAI-type-1)] complex, preferably PAI-type-1 or the complex as such, said tagging agent being preferably provided with a detectable marker preferably such as horseradish peroxidase.

one container comprising t-PA.

In particular a specific embodiment of the above-mentioned kit according to the invention comprises at least immobilized $ab_{t-PA}$ and optionally also immobilized $ab_{u-PA}$ as immobilized capturing agent(s) and antibody $ab_{PAI-type-1}$, preferably provided with a detectable marker such as horseradish peroxidase as tagging agent.

The invention is also directed at a carrier such as a microtitre plate comprising immobilized antibody directed against relevant molecular forms of t-PA and also at such a microtitre plate further comprising immobilized antibody directed against relevant molecular forms of u-PA. Said antibodies in particular being capable of binding to the molecular forms when bound in a [(PA)-(PAI-type-1)] complex.

EXAMPLES

On the basis of the findings presented further on, the following standard assay protocol was formulated:

MATERIALS AND METHODS

Human PAI-1 (lot. 02604) was purchased from American Diagnostica (Greenwich, U.S.A.); Protein A-Sepharose, Sephacryl S-300, CNBr-activated Sepharose and SPDP (N-succinimidyl 3-(pyridyldithio)propionate)) were from Pharmacia, Uppsala, Sweden; t-PA (Actilyse) from Boehringer Mannheim, horse-radish peroxidase (Grad I, 108090) from Boehringer Mannheim; TMB (3,3',5,5'-tetramethylbenzamidine) from Sigma; casein from Merck, Darmstadt, Germany; PPACK (H-D-Phe-Pro-Arg-CMK, 2.5 TFA) from Bachem-Bubendorf, Switzerland, STABILYTE tubes, containing acidic citrate were bought from Biopool, Umeä, Sweden; PBST: 0.005M phosphate, 0.13M phosphate, 0.13M NaCl, 0.05% (v/v) Tween 20, pH 7.4.

Anti-t-PA monoclonal antibody was prepared as described earlier (Bos R, Siegel K, Otter M, Nieuwenhuizen W, Production and characterization of a set of monoclonal antibodies against tissue-type plasminogen activator (t-PA). Fibrinolysis 1992; 6:173–182). The antibody, which reacts with all forms of t-PA equally well, is designated here as OT07. To find the optimum OT07 concentrations for coating, polystyrene microtitre plates were incubated with a range of OT07 concentrations from 1 to 15 µg/ml in 0.04M Tris.HCl, pH 7.4, overnight at 4° C. Plates are then washed and dried. The optimum concentration lies within 8–12 µg/ml and preferably between 9.5 and 10.5 µg/ml. In some conditions, plasma may contain [(t-PA)-(PAI-1)] and [(u-PA)-(PAI-1)] complexes. To also determine the levels of the latter in the assay, plates are coated with mixtures of OT07 and anti-u-PA monoclonal antibodies i.e. 3–10 µg/ml OT07, 2–10 µg/ml anti-u-PA, respectively.

Anti-PAI-1 polyclonal antibodies were elicited in rabbits. Rabbits were injected with a 1:1 (v/v) mixture of Freunds complete adjuvant and a solution of PAI-1 in 0.15M NaCl (concentration 50 µg PAI-1/ml). Boosts were given at 30 days intervals with a 1:1 (v/v) mixture of the same PAI-1 solution with Freunds incomplete adjuvant. Rabbit polyclonal antibodies were purified from the serum of the immunized rabbits by using Protein A-Sepharose chromatography Serum samples were diluted 2-fold in 1.5M glycine, 3M NaCl, 0.01% NaN$_3$ (w/v), pH 8.9 and applied to a Protein A-Sepharose column run in the same buffer. After washing with 5 column volumes of buffer, the antibodies were eluted with 0.1M glycine, pH 2.5, immediately neutralized with 1M Tris, pH 7.7, and dialyzed extensively in 0.1M Na$_2$HPO$_4$, 0.1M NaCl adjusted to pH 7.5 with KH$_2$PO$_4$.

The purified rabbit polyclonal antibodies were conjugated with HRP (=horseradish peroxidase) by using, the SPDP method as recommended by the manufacturer (Pharmacia). After conjugation the reaction mixture was fractionated over a SEPHACYL S-300 column run in 0.1M phosphate, 0.1M NaCl, pH 7.5. The fractions containing the conjugate were pooled and diluted to the working dilution in conjugate solvent (0.1M Na$_2$HPO$_4$.2H$_2$O; 0.03M KH$_2$PO$_4$; 0.13M NaCl, containing 0.05% (v/v) TWEEN 20 and 0.2% (w/v) casein, pH 7.5).

Concentrations of t-PA were determined essentially by using the previously described one-step enzyme immunoassay for total t-PA antigen (Bos R, Hoegee-De Nobel E, Laterveer R, Meijer P, Nieuwenhuizen W. A one-step enzyme immunoassay for the determination of total tissue-type plasminogen activator (t-PA) antigen in plasma. Blood Coagul. Fibrinol. 1992;3:303–307).

To prepare PAI-1-depleted plasma, purified anti-PAI-1 antibodies were immobilized on CNBr-activated Sepharose following the manufacturer's instructions. Plasma was depleted of PAI-1 by passing over the immobilized antibody column. All PAI-1 antigen was removed from the plasma as assessed by two different EIAS, i.e. TINTELIZA PAI-1 (Biopool, Umeå, Sweden; catalog number 210221) and INNOTEST PAI-1 (Innogenetics BA, Antwerp, Belgium).

The calibration of the reference plasma to be used in the test kit is as follows:

A sample of plasma to be used as reference containing [(t-PA)-(PAI-1)] and no free t-PA, is diluted with PBS containing 0.01M EDTA and 0.05% TWEEN 20 (PBST/EDTA). The diluted plasma is mixed with an equal volume of polyclonal anti-t-PA conjugated with HRP.

Another sample of the plasma, depleted of all t-PA antigen following the procedure described by Bos et al. (Blood Coagulation & Fibrinolysis 3 (1992) 303) is spiked with a known amount of pure t-PA. The depleted/spiked plasma is serially diluted with PBST/EDTA, and aliquots of the serial dilutions are mixed with an equal volume of polyclonal anti-t-PA conjugated with HRP.

One hundred microliter aliquots of both the putative reference plasma/polyclonal anti-t-PA-HRP conjugate mixture, and the serially diluted depleted/spiked plasma/polyclonal anti-t-PA-HRP conjugate mixtures are incubated for 3 hours at room temperature in OT07 coated wells of microtiter plates. Washing, colour development, and arresting of the reaction are done as described.

The resulting OD's of the serial dilutions of the depleted/spiked plasma are plotted against the concentration of t-PA present in the sample. The concentration of t-PA in the alleged reference plasma is read from the graph. By definition, the molar PAI-1 concentration in the reference plasma is equal to the thus found t-PA concentration, since t-PA/PAI-1 is a 1:1 complex.

ASSAY PROTOCOL samples to be determined such as blood, are collected in containers comprising means to inhibit [(PA)-(PAI-type-1)] complex formation, said means being reversible or capable of being counteracted after taking the sample. The container also comprises means for inhibiting coagulation. Means for achieving both objectives are present in STABILYTE tubes. Subsequently the sample is split in two subsamples. One subsample is routinely diluted 2-fold with PPACK-containing PBST (final PPACK concentration 30 µM) the other 4-fold with PBST. However, undiluted samples are acceptable for samples with a (expected) low PAI-1 activity level, whilst higher dilutions are acceptable for samples with (expected) high levels of PAI-1 activity and for [(t-PA)-(PAI-1)] complexes.

To 75 µl of the 4-fold diluted subsample 15 µl of a solution of t-PA in PBST is added to give a final concentration of 10 ng t-PA/ml; to the other 15 µl of PBST is added.

The samples are then mixed with 60 µl of a solution of HRP-conjugated polyclonal anti-PAI-1 antibodies in conjugate solvent.

Both subsamples are incubated for 1 hour at room temperature. One hundred µl aliquots of these mixtures are then transferred to the OT07 (see Materials and Methods) coated wells of the microtitre plates and incubated for 3 hours at room temperature.

The plates are then washed four times with PBST; TMB substrate is added and incubated for 25 minutes at room temperature.

The reaction is stopped by adding 100 µl 2N H$_2$SO$_4$, and the resulting yellow colour is measured with a multichannel spectrophotometer (Organon Teknika, Turnhout, Belgium). It is preferably to treat the portions of steps a) and c) in as similar a manner as possible in order to minimize deviations in OD values due to the presence of absence of particular compounds not relevant to the parameter to be determined.

Obviously, like in any assay of this type, calibration material is required. The following calibration procedure was found to be effective when using plasma as calibration material.

Figure 4:
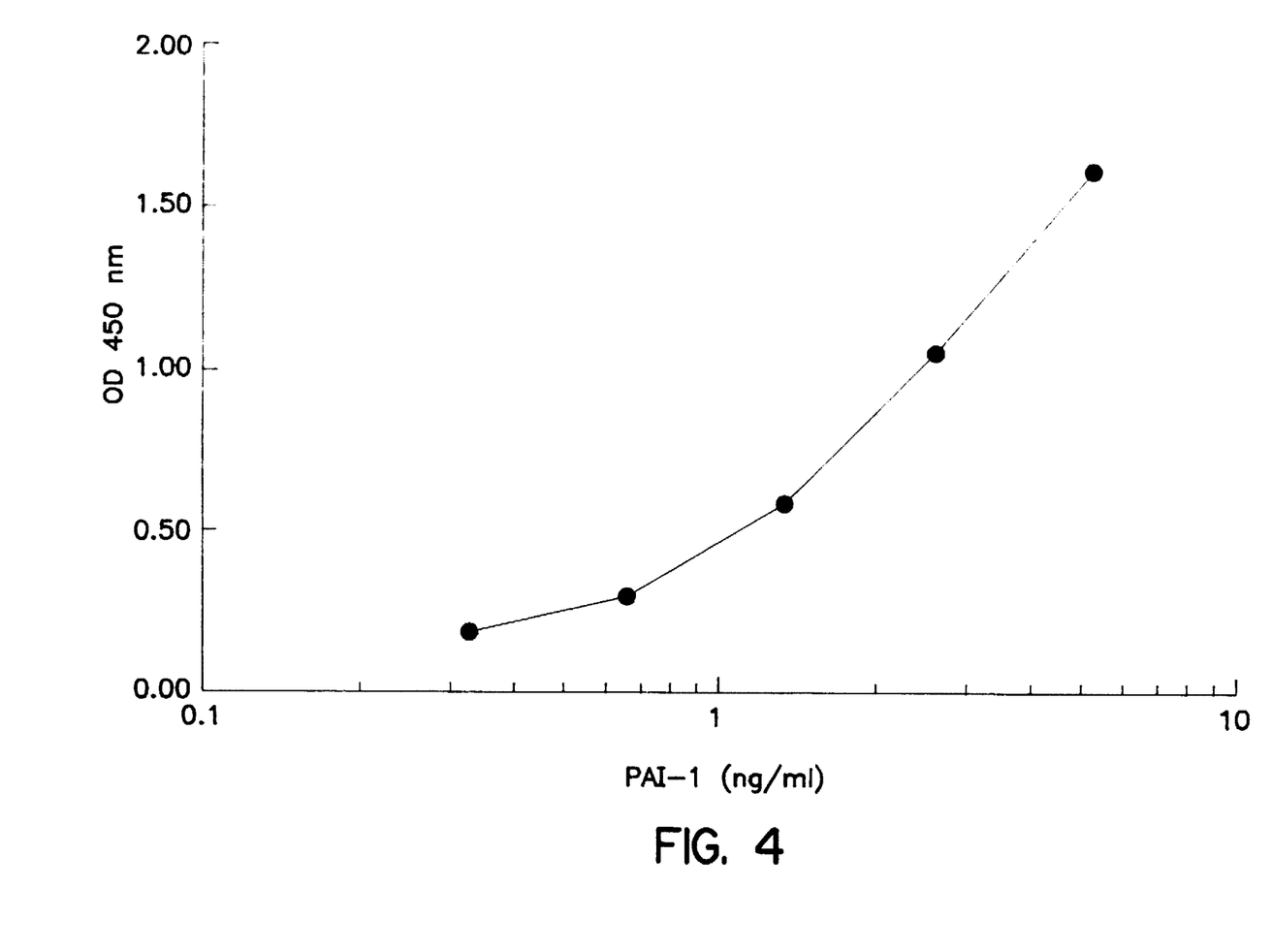
FIG. 4 illustrates a typical calibration curve for the assay according to the invention.

Pooled normal plasma to be used as calibrator was incubated for 24 hours at 37° C. to convert endogenous active t-PA to [(t-PA)-(PAI-1)] complexes. No free t-PA is present after this incubation. The amount of t-PA antigen is then assessed (Bos R, Hoegee-De Nobel E, Laterveer R, Meijer P, Nieuwenhuizen W. A one-step enzyme immunoassay for the determination of total tissue-type plasminogen activator (t-PA) antigen in plasma. Blood Coagul. Fibrinol. 1992;3:303–307) and the amount of PAI-1 in the plasma pool is calculated assuming a 1:1 complex between t-PA and PAI-1. Following the above standard protocol serial 2-fold-dilutions of the plasma pool are used to construct a calibration curve from which the PAI-1 concentrations in the unknown (sub)samples can be read. A typical calibration curve is depicted in FIG. 4.

The assay yields the amount of [(t-PA)-(PAI-1)] complex at the time of sampling; the total amount of PAI-1 which can be complexed by t-PA; and the difference between these two values which equals the amount of active PAI-1.

This assay was evaluated in a blind study of the Subcommittee on Fibrinolysis of the Scientific and Standardization Committee (SSC) of the International Society of Thrombosis and Haemostasis (Working party of Drs. Declerck, Gram, Jespersen and Kluft). The study was designed to identify possible reference methods. The criteria for a SSC reference method were: immune- and activity-depleted samples should be negative; there should be a good linearity of the assay with the PAI-1 concentration; the assay should not detect PAI-2 and PAI-3 i.e. placental PAI and urinary PAI and the change resulting from the addition of t-PA to STABILYTE plasma should be less than 20%. The samples supplied in this study are summarized in Table 1. The results obtained with these and other samples are given below.

LINEARITY

PAI-1 immune-depleted plasma spiked with 0, 4.6, 17 and 55.8 PAI-1/ml (Table 1) showed an excellent linear correlation (r=0.9998) between the added and found concentrations of PAI-1, with y=0.951X+0.01. This shows that not only the correlation but also the absolute number are in agreement with the SSC criteria.

SPECIFICITY OF THE ASSAY

Plasma samples depleted of PAI-1 antigen according to an in-house method (as assessed by two different PAI-1 antigen tests; see materials and methods) gave no response in the subject assay. However, the photometric assay described by Verheijen et al. (Verheijen J H, Chang G T G, Kluft C. Evidence for the occurrence of a fast-acting inhibitor of tissue-type plasminogen activator in human plasma. Thromb Haemostas 1984; 51:392–395) still showed a considerable apparent PAI-1 activity, which may be due to other protease inhibitors, or to the earlier described t-PA binding protein. Both the immune-depleted and the PAI-1 activity-depleted samples from the SSC study (Table 1) were negative in the subject assay.

Plasma samples from pregnant women (with elevated levels of PAI-2) and depleted of PAI-1 were negative in the subject EIA. Plasma samples depleted of PAI-1, and spiked with PAI-2 (50 ng/ml) or PAI-3 (5.5 µg/ml)(SSC study; Table 1) were negative.

The addition of t-PA to STABILYTE plasmas changes the result by much less than 20% (Table 1).

When platelet-rich (PRP) and platelet-poor (PPP) plasmas (from the same donors) were compared after freezing and thawing (to lyse the platelets) a small increase of the values for active PAI-1 in PRP as compared with PPP was found, whereas the antigen levels were considerably higher in the PRP as compared with the PPP. This is consistent with the fact that by far the majority of all PAI-1 antigen is present in platelets and in inactive form.

TABLE I

Results with samples obtained within the framework of a study of the subcommittee on Fibrinolysis of the SSC of the ISTH

| Sample | Found (U/ml) |
|---|---|
| PAI-1 activity-depleted plasma | 0 |
| PAI-1 immune-depleted plasma | 0* |
| PAI-1 immune-depleted plasma spiked with: | |
| rec-PAI-1 4.6 U/ml | 5.4* |
| rec PAI-1 17 U/ml | 17.1* |
| rec PAI-1 55.8 U/ml | 58.8* |
| PAI-1 immune-depleted plasma spiked with 50 ng PAI-2/ml | 0 |
| PAI-1 immune-depleted plasma spiked with 5.5 µg PAI-3/ml | 0 |
| 1 Stability ® plasma 1 (11 IU PAI-1/ml) | change = 0.1 U/ml (1 minus 2) |
| 2 Stability ® plasma 1 spiked with 16 IU t-PA/ml) | |
| 3 Stability ® plasma 2 (16 IU/PAI-1/ml) | change = +0.4 U/ml (3 minus 4) |
| 4 Stability ® plasma 2 spiked with 7 IU t-PA/ml | |

*for this concentration range an r = 0.9998 and y = 0.95% + 0.01 were found

It is known that PAI-1 loses its activity upon incubation at 37° C. To assess if this process can be followed with the subject assay, aliquots of the same plasma were incubated at different temperatures for different periods of time. Then the levels of active PAI-1 (the subject assay), PAI-1 antigen (Innotest, Innogenetics, Belgium) and the apparent PAI-1 activity (spectrophotometric assay as described by Verheijen J H, Chang G T G, Kluft C. Evidence for the occurrence of a fast-acting inhibitor of tissue-type plasminogen activator in human plasma. Thromb Haemostas 1984; 51:392–395) were determined.

The amounts of antigen are found to be independent of time and temperature of incubation. The two PAI-1 activity tests show a decline particularly at 37° C. However, the apparent half-life of PAI-1 activity as assessed by the spectrophotometric assay is much shorter than observed with the subject assay. This may be due to other protease inhibitors than PAI-1 which are also detected in the spectrophotometric assay and not in the subhect EIA. With the subject EIA the apparent half lives of PAI-1 activity are 2 hours, 23 hours, and >24 hours at 37° C., 18° C., and 40° C., respectively, which is in fair agreement with the values found by Philips et al. (Philips M. Juul A G, Seimer J, Lind B, Thorsen S. A specific immunologic assay for functional plasminogen activator inhibitor-1 in plasma. Standardized measurements of the inhibitor and related parameters in patients with venous thromboembolic disease. Thromb Haemostas 1992; 68:486–494), who found 2.3, 20 and 117 hours, respectively.

It has been observed that special precautions such as the prevention of the reaction between t-PA and PAI-1 are not required when using plasma from normal resting donors (Philips M. Juul A G, Seimer J, Lind B, Thorsen S. A specific immunologic assay for functional plasminogen activator inhibitor-1 in plasma. Standardized measurements of the inhibitor and related parameters in patients with venous thromboembolic disease. Thromb Haemostas 1992; 68:486–494). The observations were confirmed (not shown) by performing the assay with and without PPACK in the subsample which is not incubated with t-PA. Minor differences were observed, the apparent levels of active PAI-1 being on average 10% lower when PPACK was not used. However, for patients with increased levels of t-PA the means for stopping complexation for the sample portion of step a) is definitely necessary in order to achieve accurate results.

REPRODUCIBILITY OF THE ASSAY

The intra-assay variability was assessed by measuring two independent plasmas in six-fold. The two samples contained (average) 8.8 and 14.4 ng active PAI-1 per ml. Their intra-assay CV's were 4.5 and 8.3%, respectively.

By measuring the same samples on four different days (single determinations) values of (average) 9.1 and 14.1 ng active PAI-1 were found, with inter-assay CV's of 5.5 and 6.4%, respectively.

Samples with very low levels of PAI-1 (in the order of 1 ng/ml) yield results with a rather high CV (around 30%). Such samples should be re-assessed at lower dilutions than in the standard procedure (see above).

NORMAL ACTIVE PAI-1 LEVELS

In 16 normal healthy donors plasma active PAI-1 levels were found ranging from 0.6–18.6 ng/ml. PAI-1 levels in the form of t-PA/PAI-1 complexes ranged from 1.1 to 9.5 ng/ml. The sensitivity is better using the assay of the subject invention than in the cited European application 0 450 086.

BLOOD COLLECTION

When blood is taken from normals on citrate, or EDTA as anticoagulant, centrifuged, and stored at −80° C. immediately, no special precautions are required to prevent conversion of active PAI-1 to t-PA/PAI-1 complexes. Since the assay will also be used to assess levels in patients, where the haemostatic balance may be severely disturbed such means are required and the use of STABILYTE tubes (acidic citrate) is preferred. The buffers used in the example of the subject assay correct the pH to around 7.4 in the assay. The buffer should result in a pH at which immune reaction can be efficiently carried out. An additional advantage of the use of STABILYTE tubes lies in the stabilizing effect on blood platelets, preventing release of latent PAI, present in a very high percentage in platelets into the plasma thereby eliminating a potential source of inaccurate measurement.

I claim:

1. A method for the quantification of active plasminogen-activator-inhibitor-type-1 (PAI-type-1) present in a sample, comprising taking two portions from a sample,
   a) determining in one portion a value corresponding to the total amount of complex between PAI-type-1 and plasminogen activator (PA), the (PA)-(PAI-type-1) complex, being the total complex with plasminogen activator (PA) already present at the moment of sampling;
   b) calculating from the value determined in step a) the amount of (PA)-(PAI-type-1) complex present at the moment of sampling;
   c) determining in the other portion a value corresponding to the total amount of (PA)-(PAI-type-1) complex present after addition of an excess of the active form of tissue-type plasminogen activator (t-PA) to said portion;
   d) calculating from the value determined in step c) the amount of (PA)-(PAI-type-1) complex present after the addition of the excess t-PA;
   e) subtracting the total amount of complex as determined in b) from the total amount of complex as determined in d), resulting in the amount of active PAI-type-1 that was present at the moment of sampling in a volume of the sample equivalent to the volume of the portion, wherein the portion of step a) is contacted with means for inhibiting complexation of PA with PAI-type-1 from the moment of sampling through step a) and step a) comprises contacting the portion with at least one immobilized capturing agent, said immobilized capturing agent i) being directed at PA, and ii) being present in an amount and with a specificity sufficient for the molecular forms of PA present in the portion to be complexed to said capturing agent and contacting the portion with at least one tagging agent, said tagging agent being directed at PAI, and being present in an amount and with a specificity for the molecular forms of PAI-type-1 present in the portion to be complexed to said tagging agent and subsequently, after carrying out incubation and a washing step, determining a value corresponding to an amount of tagging agent that has been immobilized by binding to immobilized capturing agent, and wherein step c) comprises contacting the other portion with an excess of the active form of t-PA, thereby allowing any non-bound active PAI-type-1 present in the portion before the addition to form a (PA)-(PAI-type-1) complex and also contacting this portion with tagging agent and capturing agent as set forth in step a), and subsequently determining a value corresponding to the amount of tagging agent that has been immobilized by binding to the immobilized capturing agent.

2. The method according to claim 1, wherein the capturing agent is an antibody having binding affinity for different molecular forms of t-PA selected from single chain t-PA, double chain t-PA and (t-PA)-PAI-type-1) complex.

3. The method according to claim 1, wherein the tagging agent is an antibody directed against PAI-type-1.

4. The method according to claim 1, further comprising a second capturing agent capable of binding different molecular forms of urokinase plasminogen activator selected from single chain u-PA, double chain u-PA and (u-PA)-(PAI-type-1) complex.

5. The method according to claim 1, wherein the capturing agent directed against PA binds to the molecular form of the corresponding (PA)-(PAI-type-1) complex.

6. The method according to claim 3, wherein the tagging agent is an antibody directed against PAI of the (PA)-(PAI-type-1) complex.

7. The method according to claim 1, wherein the means for inhibiting complexation of PA with PAI-type-1 from the moment of sampling through step a) comprises changing the pH of the sample to an acidic level at which the complexation is inhibited or comprises adding an inhibitor of PA.

8. The method according to claim 1, wherein the portion to be used in step c) is first subjected to a means to inhibit complexation of PA with PAI-type-1 from the moment of sampling until, just prior to step c), is then subjected to an additional means to reverse the inhibition of complexation.

9. The method according to claim 8, wherein the means for inhibition of complexation comprises means for maintaining a sufficiently acidic pH and the means for reversing the inhibition comprises an alteration of the acidic pH to a level at which capturing and/or tagging can occur.

10. The method according to claim 1, wherein prior to steps a) and c) the portions are subjected to means rendering immune reactions possible, thereby concomitantly ensuring that complexation in step a) to (PA)-(PAI-type-1) remains inhibited, said means comprising amending the pH in step a) to a level at which capturing and/or tagging can occur with addition to the portion of step a) of an inhibitor of t-PA to ensure inhibition of complexation.

11. The method according to claim 1, wherein the tagging agent has a detectable marker, and the detectable marker is an enzyme having a chromogen as substrate and a chromophore as product.

12. The method according to claim 1, wherein the capturing agent is immobilized in the well of a microtiter plate.

13. The method according to claim 1, wherein the amount of immobilized tagging agent is determined by measuring the O.D. value of the sample.

14. The method according to claim 1, further comprising in steps b) and d) calculating the amounts of (PA)-(PAI-type-1) complex from the respective values obtained in steps a) and c) by comparison of said respective values with corresponding values on a reference curve, said reference curve being a plot of known concentrations of (PA)-(PAI-type-1) complex against the corresponding O.D. value produced by the immobilized tagging agent.

15. The method according to claim 14, wherein said reference curve is obtained by using at least one reference sample, said reference sample comprising a known concentration of (PA)-(PAI-type-1) complex, and/or by using one or more dilutions of said reference sample to carry out step a) or c), thereby obtaining at least two values corresponding to two specific concentrations of (PA)-PAI-type-1) complex and plotting the values determined against their respective known concentrations.

16. A method for determining the specific known concentration of (PA)-(PAI-type-1) complex in a reference sample comprising performing the method of claim 1, on the sample.

17. A method comprising the following steps:
    a) subjecting a reference sample to conditions such that virtually all t-PA present in the reference sample is converted to (t-PA)-(PAI-type-1) complex,
    b) making a serial dilution of the mixture resulting from step a) resulting in subsamples,
    c) contacting the subsamples formed in step b) with at least one immobilized capturing agent for one of the components of the (PA)-(PAI-type-1) complex, resulting in an immobilized (PA)-(PAI-type-1 complex,
    d) contacting the immobilized complex from step c) with at least one tagging agent for one component of the immobilized complex,
    e) measuring each subsample to obtain the value corresponding to the amount of immobilized tagging agent per subsample and
    f) plotting the values obtained in step e) against the amount of marker corresponding to said value, the amount of marker being derivable from a calibration curve for said marker and the component of the (PA)-(PAI-type-1) against which the tagging agent is directed, for determining the specific known concentration of (PA)-(PAI-type-1) complex in the reference sample to be used in the method according to claim 15.

18. The method of claim 17, wherein the tagging agent is directed against t-PA.

19. The method of claim 17, wherein the tagging agent comprises a detectable marker.

20. The method of claim 19, wherein in step c) an immobilized capturing agent for t-PA is used, resulting in an immobilized (t-PA)-(PAI-type-1) complex and in step d) the immobilized complex from step c) is contacted with a tagging agent for relevant molecular forms of t-PA as comprised in the immobilized (t-PA)-(PAI-type-1) complex, said tagging agent being provided with the same detectable marker.

21. A kit comprising components for carrying out a method according to claim 1, comprising:
    one sample with a known amount of (PA)-(PAI-type-1) complex;
    a carrier comprising at least one immobilized capturing agent directed against PA or against the (PA)-(PAI-type-1) complex;
    at least one tagging agent directed against PAI or against the (PA)-(PAI-type-1) complex, said tagging agent being provided with a detectable marker; and
    t-PA.

22. A kit according to claim 21, comprising an immobilized antibody directed against t-PA.

23. A kit according to claim 21, further comprising phosphate buffer.

24. A carrier comprising immobilized antibody directed against t-PA.

* * * * *